(12) United States Patent
Schnabelrauch et al.

(10) Patent No.: US 8,414,958 B2
(45) Date of Patent: Apr. 9, 2013

(54) IMPLANT AND METHOD FOR THE MANUFACTURE THEREOF

(75) Inventors: Matthias Schnabelrauch, Jena (DE); Armin Rex Kautz, Jena (DE); Falko Schlottig, Füllinsdorf (DE)

(73) Assignee: Thommen Medical AG, Waldenburg (CH)

( * ) Notice: Subject to any disclaimer, the term of this patent is extended or adjusted under 35 U.S.C. 154(b) by 0 days.

(21) Appl. No.: 12/919,678

(22) PCT Filed: Feb. 23, 2009

(86) PCT No.: PCT/EP2009/052112
§ 371 (c)(1),
(2), (4) Date: Nov. 19, 2010

(87) PCT Pub. No.: WO2009/106502
PCT Pub. Date: Sep. 3, 2009

(65) Prior Publication Data
US 2011/0053113 A1  Mar. 3, 2011

(30) Foreign Application Priority Data
Feb. 27, 2008 (CH) ........................... 0281/08

(51) Int. Cl.
*A61L 33/00* (2006.01)

(52) U.S. Cl. ....... 427/2.24; 424/426; 424/400; 424/472; 549/292; 514/311; 514/256; 514/423; 514/419; 514/460; 514/548; 514/560; 623/1.46

(58) Field of Classification Search ................. 623/1.46, 623/1.42; 514/256, 311; 549/292; 424/400, 424/426
See application file for complete search history.

(56) References Cited

U.S. PATENT DOCUMENTS

| 4,916,239 | A * | 4/1990 | Treiber ........................ 549/292 |
| 6,380,401 | B1 * | 4/2002 | McManus et al. ........... 549/292 |
| 6,545,097 | B2 | 4/2003 | Pinchuk et al. |
| 2004/0132771 | A1 * | 7/2004 | Babcock et al. .............. 514/311 |
| 2004/0247673 | A1 | 12/2004 | Fergione et al. |
| 2005/0070997 | A1 * | 3/2005 | Thornton et al. ............ 623/1.46 |
| 2006/0193893 | A1 * | 8/2006 | Brown .......................... 424/426 |
| 2007/0048351 | A1 | 3/2007 | Lunn |
| 2007/0254897 | A1 * | 11/2007 | Gjorstrup ..................... 514/256 |
| 2009/0130177 | A1 | 5/2009 | Schlottig et al. |
| 2009/0196889 | A1 * | 8/2009 | Penhasi ......................... 424/400 |

FOREIGN PATENT DOCUMENTS

| DE | 201 22 679 U1 | | 3/2007 |
| EP | 1880690 | * | 7/2000 |
| EP | 1 159 934 A2 | | 12/2001 |
| WO | 03/105731 A1 | | 12/2003 |
| WO | 2004/091626 A1 | | 10/2004 |
| WO | WO 2005/009431 | * | 3/2005 |
| WO | 2006/082500 A1 | | 8/2006 |
| WO | 2007/048264 A1 | | 5/2007 |

OTHER PUBLICATIONS

Fatma A. Ismail, "Design and In Vitro Evaluation of Polymeric Formulae of Simvastatin for Local Bone Induction", Drug Development and Industrial Pharmacy, Nov. 2006, pp. 1199-1206, vol. 32, No. 10, DOI: 10.1080/03639040600751886, XP009090743.

* cited by examiner

*Primary Examiner* — Dah-Wei Yuan
*Assistant Examiner* — Andrew Bowman
(74) *Attorney, Agent, or Firm* — Sughrue Mion, PLLC

(57) ABSTRACT

What is described is an implant that comprises a coating, at least in areas, in the implanted state in the surface areas that are at least directly in contact with skin and/or soft tissue. The implant is preferably characterized in that the coating comprises both a statin, such as simvastatin, in the hydrolyzed or unhydrolyzed form, or pharmaceutically compatible salts thereof, as well as at least one other component selected from the group consisting of branched or linear, substituted or unsubstituted, saturated or partially unsaturated C10-C30 alkyl, alkenyl, alkylaryl, aryl, cycloalkyl, alkylcycloalkyl, alkylcycloaryl amines or mixtures thereof and/or at least one water-soluble ionic polymer component. A method for production such an implant is also described as well as a composition that can be used in such a method.

28 Claims, No Drawings

IMPLANT AND METHOD FOR THE MANUFACTURE THEREOF

This application is a National Stage of International Application No. PCT/EP2009/052112 filed Feb. 23, 2009, claiming priority based on Swiss Patent Application No. 00281/08, filed Feb. 27, 2008, the contents of all of which are incorporated herein by reference in their entirety.

TECHNICAL FIELD

The present invention relates to a process for producing an implant, especially a dental implant, and to an implant produced thereby, which has a coating which, in the implanted state, is in at least some of the surface regions which are in contact with hard and/or soft tissue.

STATE OF THE ART

For the functional restoration of hard tissue in the human body after injuries, for example for fractures, abrasions or the removal of malignant tumors, synthetic materials are increasingly being used as permanent or temporary replacement materials. In this case, these replacement materials in the form of implants should primarily replace the lost body functions as far as possible.

Particular demands are made on the implants both with regard to the structure and with regard to the surface thereof. The mechanical properties, such as structure and geometry of the implants, make a significant contribution to the mechanical stability of the implants. The nature of the surface is important for the growth of the implant into the bone. The stability of the implant in the hard tissue depends crucially on the interactions at the implant surface/surrounding tissue interface, and on the microscopic and macroscopic morphology of the implant. For instance, a change to the implant surface can improve the anchoring of the implant in the hard tissue, and also the implant compatibility, hence enhancing the osseointegration of the implant, which accelerates the healing process.

The osseointegration of the implant into the bone can be improved by processing of the implant surface. Possible methods of surface treatment include sandblasting and/or treatment with an acid, which lead to roughening of the implant surface. Further possible options include plasma spraying processes, and electrochemical processes or dipping processes, by which different, often porous layers can be applied to the surface of the implants. However, the osseointegration of implants can also be enhanced by a biological functionalization of the surface thereof. This involves applying a molecular layer of the active ingredient to a pretreated surface by means of a chemical bond.

In the last few years, different pharmaceutical coatings of the implant surface have been developed, which release the active ingredient to the tissue surrounding the implant and thus promote the incorporation of the implant and hence support the healing process. The coating materials used for such implants may, for example, be proteinogenic growth factors, or else pharmaceuticals which are administered for the systemic treatment of degenerative bone disorders such as osteoporosis. Many of the medicaments used here, such as bisphosphonates, calcitonin and estrogen, inhibit bone absorption and thus contribute to bone formation, while bone morphogenetic proteins (BMP), like the recombinant human bone morphogenetic protein 2 (rhBMP-2) stimulate the formation of new bone.

It has been reported recently that statins such as simvastatin (INN) can promote the formation of bone in vitro, and also in vivo. Simvastatin in particular is a fat-soluble representative from the group of the statins. Statins belong to the pharmacological substance class of the 3-hydroxy-3-methylglutaryl-coenzyme A reductase (HMG-CoA reductase) inhibitors, and block the conversion of β-hydroxy-β-methylglutaryl-coenzyme A to mevalonate, the rate-determining step in the synthesis of human cholesterol. These medicaments are strong inhibitors of cholesterol biosynthesis and are administered, for example, to lower cholesterol in patients with metabolic disorders. In addition, they are used for treatment of cardiovascular disorders, for example atherosclerosis, and in the case of acute myocardial infarction. The examples of statins in clinical use include atorvastatin, fluvastatin, lovastatin, pravastatin, rosuvastatin and simvastatin.

In chemical terms, simvastatin is [(1S,3R,7R,8S,8aR)-8-[2-[(2R,4R)-4-hydroxy-6-oxo-oxan-2-yl]ethyl]-3,7-dimethyl-1,2,3,7,8,8a-hexahydronaphthalen-1-yl] 2,2-dimethylbutanoate.

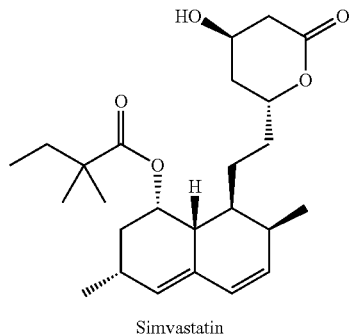 [SMILES: CCC(C)(C)C(=O)O[C@H]1C[C@@H](C)C=C2C=C[C@H](C)[C@H](CC[C@@H]3C[C@@H](O)CC(=O)O3)[C@H]21]

Simvastatin

Simvastatin is commercially available in the lactone form (cf. figure above). However, simvastatin possesses physiological action in the metabolically active form, known as the open-chain or β-hydroxy acid form, to which it first has to be converted from the lactone form. Synthesis methods for the opening of the lactone ring are known to those skilled in the art.

As has been demonstrated, BMP-2 is responsible for the differentiation of a multipotent stem cell line into osteoblast-like cells. BMPs are thus important regulators in the differentiation of bone cells during the healing of broken bones. In order to study which small molecules induce BMP-2, more than 30 000 compounds were studied, and the effect thereof on the expression of the genes for BMP-2 was tested. It was found that statins enhance this expression of BMP-2 mRNA. The pharmacological action of the statins is thus probably attributable to enhanced expression of the genes for BMP-2 in bone cells.

The inductive effect of simvastatin on the new formation of bones has already been studied. For these in vitro and in vivo studies, different administration forms were used for the administration of the simvastatin.

For example, pure titanium implants were implanted into the tibias of rats, and the simvastatin was administered daily into the abdominal cavity. In the animals thus treated, thicker trabecular bone with a network-like structure was found in the medullar channel. Studies of the bone contact ratio to the implant and of the bone density around the implant show a significant increase. Since simvastatin here, however, acts systemically, very high doses are required to stimulate only bone growth.

Simvastatin has already also been used with calcium sulfate as a carrier material, which is biocompatible and bioabsorbable. To this end, the two powders were mixed and shaped to disks which were inserted into the bones of rats. Eight weeks after the introduction of the disks containing simvastatin, a significant increase in the bone density, in the mineral content of the bones and in the bone mineral density was observed compared to the control group receiving only calcium sulfate or neither substance.

Other matrices used for simvastatin have been collagen and gelatin. In this case, collagen sponges composed of purified bovine collagen, which had been impregnated with an aqueous simvastatin solution, were used to treat fractures in the parietal bone of rabbits. Growth factors which are important for the healing of the bones were detected at an earlier stage as a result. Simvastatin initiated the early expression of the growth factors, the differentiation of the bone cells and osteogenesis, which led to accelerated formation of new bone. For the treatment of fractures in jawbones of rats, in addition, simvastatin was already introduced into gelatin sponges. Here too, the bone density was 190-240% above that of the control group receiving no active ingredient. In histological studies, enhanced formation of new bone was detectable.

The in vitro release of simvastatin from granules and gels has likewise already been studied. The starting materials used for the granules and gels were the biocompatible and degradable polymers hydroxypropylmethylcellulose and carboxymethylcellulose. After 24 hours, the release profile showed cumulative release of simvastatin in the case of granules and gels. In these studies, the polymers and simvastatin were merely mixed to produce the granules, soaked with different mixtures of alcohol and water or dilute lactic acid and forced through a sieve, and then dried. This afforded granules having a size of 800-1500 μm. For the preparation of the gels, the polymers were dispersed stepwise in water, this polymer dispersion was frozen and the simvastatin was applied to the gel system before the start of the release. In this procedure, no interactions can form between the simvastatin and polymeric systems present alongside one another, which is manifested in the rapid release within the first 24 hours.

A further combined use of simvastatin in this case together with an NO-providing system and a phosphodiesterase (PDE) system for controlling bone growth is described in WO 2004/091626, and one suggestion made is that such a combination preparation for controlled release of the active substances can be introduced into the films, which can subsequently be wound around implants before the incorporation thereof.

EP 1159934 describes a tubular deformable implant which may bear a "medicine", it being possible to provide at least part of this implant with a coating material consisting of a biocompatible material, a biodegradable material or a synthetic resin. The coating material described may consist of a biodegradable material to which a "medicine", a bioprosthetic material or a biosynthesis material may be added. The coating material is one consisting of a biocompatible material, a biodegradable material or a synthetic resin. The situation is analogous for U.S. Pat. No. 6,545,097: a polymeric composition composed of synthetic block copolymers is disclosed, which can be used to release active therapeutic ingredients, for example in the form of a coating. With reference to the disclosed composition of the synthetic block copolymers, it can be assumed that this material can only be dissolved exceptionally slowly, if at all, in the body, and hence remains in the organism permanently or at least over a very long period. The invention therefore intrinsically harbors all disadvantages known from polymeric coating systems, and does not disclose an alternative solution to this problem.

US 2007/0048351 discloses a method for treatment of plaque formation in vessels by introducing a tubular shaped body comprising one or more active ingredients, the active ingredient being applied to the implant surface alone or in combination with a polymer. The statements made above apply to the case of use of polymers in combination with the active ingredient.

DESCRIPTION OF THE INVENTION

The invention relates to the production of an improved implant, preferably of a dental implant, which has good osseointegration and osteointegration, and can nevertheless be produced in a simple and inexpensive process.

In other words, the invention comprises the improvement of a process for producing an implant which has a coating which, in the implanted state, is in at least some of the surface regions which are in at least indirect contact, but preferably in direct contact, with hard and/or soft tissue.

The improvement is especially achieved by virtue of the coating comprising both a statin in the hydrolyzed or unhydrolyzed form, or pharmaceutically compatible salts thereof, and at least one further component selected from the group of the branched or linear, substituted or unsubstituted, saturated or partly unsaturated C10-C30 alkyl-, alkenyl-, alkylaryl-, aryl-, cycloalkyl-, alkylcycloalkyl- or alkylcycloarylamines or mixtures thereof, and/or at least one water-soluble ionic polymeric component.

In the coating, the statin is present in the form of a pharmaceutically compatible salt derived from an open-chain, biologically active dihydroxy acid form with at least one further component. It is only the dihydroxy acid form that enables the formation of mixed salts with the components listed above.

Preferably, at least one layer of the coating (or the whole coating) consists of such a layer, essentially without further constituents. More particularly, there is no coating material consisting of a biocompatible material, a biodegradable material or a synthetic resin.

A fundamental distinguishing feature from the prior art consists in the fact that no coating material consisting of a biocompatible material, a biodegradable material or a synthetic resin is used, and the particular chemical structure of the active ingredient component (low molecular weight or polymeric, low-water-solubility ammonium salt) instead allows such a coating material to be dispensed with entirely, thus allowing all known and demonstrated disadvantages of such materials (including uncontrolled degradation, reactions to foreign bodies, flaking of polymer particles out of the coating) to be avoided. The particular chemical structure of the active ingredient salts ensures that the active ingredient component adheres to the implant surface, which cannot normally be assumed in the case of conventional active ingredients and therefore necessitates the use of additional coating materials.

The prior art, for example EP 1159934, with regard to the application of pharmaceuticals to implant surfaces, merely restates the prior art known from many publications and patents, without going any further. This is also illustrated specifically by example 2, where a coating in which a mixture of the active ingredient (cerivastatin) and of a polymer (polylactide) in an organic solvent is used. It is also evident from the description of the background to this document that the field of use relates essentially to the treatment of vascular stenoses or occlusions, where an antiproliferative effect is to be achieved. The field of use of this invention, in contrast, relates to an improvement in the incorporation behavior of implants into the surrounding tissue, i.e. a stimulation of the proliferation of surrounding cells. The application of an antiproliferative implant coating to a coating which is intended to induce proliferation-promoting action is not obvious.

Generally, in the context of the present invention, a statin is understood to mean a statin as such; this is preferred. However, it is also understood to mean a component which acts in the same way as a statin, i.e. a component, for example apamine or zaragozic acid, which is likewise effective in the context of the isoprenoid/steroid pathway, but does not directly influence the targets of the statins as such (i.e. HMG-CoA reductase).

The statin may in principle be present in hydrolyzed or unhydrolyzed form at the end; it may thus have a closed or open lactone ring.

More particularly, the proposed coating is notable in that, after insertion into the human or animal bone, it releases the statin, preferably simvastatin, to the environment in a retarded manner.

The statin is preferably a component selected from the following group: atorvastatin, cerivastatin, fluvastatin, lovastatin, pitavastatin, pravastatin or rosuvastatin, mevastatin, squalestatin, simvastatin, or a mixture of such components. The statin is most preferably simvastatin.

In a first preferred embodiment, the statin and the further component and/or the water-soluble ionic polymeric component are present in the coating as a complex or mixed salt with low solubility in water. The complex or the mixed salt preferably has a solubility in pure water of less than 1 mg/ml at room temperature, preferably in the range of less than 0.05-0.9 mg/ml at room temperature.

In a further preferred embodiment, the further component is at least one unbranched, preferably unsubstituted, C10-C20 alkylamine (the amine may be substituted), and/or the alkali metal or alkaline earth metal salt thereof, preferably selected from the following group: decylamine, tetradecylamine, hexadecylamine, octadecylamine, dodecylamine.

The further component is preferably an amphiphilic component. The further component preferably has cationic character, and especially preferably bears a single positive charge.

In a further preferred embodiment, the implant is characterized in that the statin is present in the free dihydroxy acid form and preferably at least partly in the alkali metal, alkaline earth metal, ammonium and/or magnesium salt form and/or salt form with the further component as the ammonium cation.

With regard to the water-soluble ionic polymeric component, it is preferred that the water-soluble ionic polymeric component is a polymeric component with free cationic groups, especially a polymeric component which derives from biologically compatible biopolymers. The water-soluble ionic polymeric component may preferably comprise amino-containing derivatives of natural polysaccharides, especially preferably polysaccharides selected from the group of: dextran, cellulose, starch, pullulan or chitosan, or mixtures thereof.

The statin preferably present in the free dihydroxy acid form and the further component preferably selected as the alkylamine are preferably present in the coating in a molar ratio between 10:1 and 1:5, preferably in a molar ratio of 2:1 to 1:2.

The statin preferably selected in the free dihydroxy acid form and the water-soluble ionic polymeric component in the coating are preferably present in a molar ratio between 10:1 and 1:5, preferably in a molar ratio of 2:1 to 1:2, based in each case on the carboxyl groups of the statin used in the free dihydroxy acid form and the cationic groups present in the polymeric component.

A further preferred embodiment is characterized in that the coating is applied to a smooth, porous and/or roughened surface without a carrier, the implant preferably consisting at least partially or in sections of metal and/or ceramic and/or polymers and/or being of native origin, and the coating especially preferably being applied directly and without an intermediate layer to such an implant, and the implants preferably comprising calcium phosphate ceramics, aluminum oxide and zirconium oxide ceramics, bioglass, glass ceramics, calcium carbonate, calcium sulfate, organic polymers or composites of the materials mentioned, or surfaces of metallic implants made from pure titanium, titanium alloys, cobalt-chromium alloys or stainless steel, or native implant surfaces which consist of collagen, gelatin or materials of allogenic origin.

The thickness of the coating is typically between 1-10 μm, preferably 0.5-5 μm.

The coating is preferably a dry, essentially solvent-free coating which is essentially water-free before implantation.

A further preferred embodiment is characterized in that the coating is applied as a slurry or suspension in an organic solvent, optionally in a mixture with water, preferably in a dipping or spraying process, and is then dried substantially completely.

The implant is preferably a dental implant.

The present invention thus relates to a process for producing an implant as described above. This process is preferably characterized in that either a suspension and/or solution of the statin and of the at least one component and/or of the water-soluble ionic polymeric component is prepared in a suspension medium or solvent, in that the coating is applied to the implant surface to be coated by spray application, dropwise application or dipping of this suspension or solution, and in that the suspension medium or solvent is removed, preferably by evaporation or vaporization, to form a low-water-solubility, statin-containing, dry coating.

In an alternative variant of this process, the procedure is to prepare a first suspension and/or solution of the at least one component and/or of the water-soluble ionic polymeric component in a suspension medium or solvent, and a second suspension and/or solution of the statin in a suspension medium or solvent, to apply the first or the second suspension and/or solution to the surface to be coated by spray application, dropwise application or dipping, and to remove the suspension medium or solvent, preferably by evaporation or vaporization, and then to apply the other suspension and/or solution to the surface to be coated by spray application, dropwise application or dipping, and to remove the suspension medium or solvent, preferably by evaporation or vaporization, to form a low-water-solubility, statin-containing, dry coating.

A first preferred embodiment of the process proposed is characterized in that the concentrations of the suspension(s) and/or solution(s) which comprise the statin and/or the further component and/or ionic polymeric component are selected such that the statin and the further component and/or ionic polymeric component are present in the coating formed by in situ salt formation in a ratio of 10:1 to 1:5, preferably between 2:1 and 1:2.

The suspension and/or solution which contains the statin and the further component and/or ionic polymeric component is preferably prepared by mixing a dihydroxy acid form of the statin dissolved in at least one alcohol or an alcohol-water mixture, preferably in a ratio of 25:75, and a further component and/or water-soluble ionic polymeric component dissolved in at least one alcohol or an alcohol-water mixture, isolating the precipitation product as a mixed salt, and then dissolving or suspending this mixed salt in a solvent or suspension medium.

The suspension medium or solvent may generally be a suspension medium mixture or solvent mixture.

A further preferred embodiment of the process proposed is characterized in that the suspension medium or solvent used is water or one or more organic suspension media or solvents, preferably chloroform as the suspension medium or ethanol and/or methanol as the solvent, or mixtures of these systems where chemically possible with regard to miscibility.

The coating is preferably applied as a suspension or slurry in an organic solvent, preferably in a spraying or dipping process, and then dried completely.

The present invention additionally relates to a statin-containing composition in the sense of the above-specified suspension/solution. This composition is in the form of a mixed salt which has low solubility in an aqueous medium and comprises both a statin with closed or open lactone ring, preferably selected from the group of atorvastatin, cerivastatin, fluvastatin, lovastatin, pitavastatin, pravastatin, mevastatin, squalestatin, rosuvastatin, simvastatin, or pharmaceutically compatible salts thereof, and at least one further component selected from the group of the branched or linear, substituted or unsubstituted, saturated or partly unsaturated C10-C30 alkyl-, alkenyl-, alkylaryl-, aryl-, cycloalkyl-, alkylcycloalkyl- or alkylcycloarylamines or mixtures thereof, and/or a water-soluble ionic polymeric component.

With regard to the statin, the further component, and likewise the water-soluble ionic polymeric component, the preferred embodiments specified above in connection with the implant apply, i.e. these are explicitly also described and disclosed in connection with the composition claimed.

For example, a first preferred embodiment of the composition is characterized in that the mixed salt has a solubility at room temperature in pure water of less than 1 mg/ml, especially preferably in the range of less than 0.05-0.9 mg/ml, at room temperature.

A further preferred embodiment of the composition is, for example, characterized in that the further component is at least one unbranched, preferably unsubstituted, C10-C20 alkylamine and/or alkali metal or alkaline earth metal salt thereof, preferably selected from the following group: decylamine, tetradecylamine, hexadecylamine, octadecylamine, dodecylamine.

Another preferred embodiment is, for example, characterized in that the water-soluble ionic polymeric component comprises amino-containing derivatives (e.g. diethylaminoethyl, ethylenediamino or amino groups) of natural polysaccharides, especially preferably polysaccharides selected from the group of: dextran, cellulose, starch, pullulan or chitosan, or mixtures thereof.

In addition, the present invention relates to the use of a composition as described above in the context of a process as described above, i.e. for coating metallic, nonmetallic or native implant surfaces, said implant surfaces especially preferably being smooth, structured and/or porous, and said implant preferably being a dental implant.

In summary, it can be stated that the aim of the invention is achieved by virtue of the dental implant having a specific coating in the region of the surface in which, in the implanted state, it is in contact with the hard and/or soft tissue. The contact with hard and/or soft tissue may be direct or else indirect via openings, channels and/or a further layer or layers. The release of the statin, especially preferably of the simvastatin, should be altered only slightly, if at all, by the surface structure described. The coating comprises at least one statin and preferably amino-containing water-soluble ionic polymers and/or alkanes.

In addition, mixtures of different statins and mixtures of different amino-containing water-soluble ionic polymers and/or alkanes are possible.

The invention is based essentially on the fact that statins would be transported very rapidly away from the surface of the implants after the incorporation thereof, whereas a mixed salt of the above-specified components fixes the statins for a longer period at the interface between implant and surrounding hard and/or soft tissue after the introduction of the implant into the human or animal body, as a result of which they can exert their effect over a longer period. By virtue of the appropriate selection of the individual components of these mixed salts, after coating of the dental implants, release of the statins and hence the bioavailability thereof on the surface of the implants and in the direct environment thereof over several days to weeks can be achieved. According to this invention, the two constituents of the coating are present as a mixture or complex, preferably as a mixed salt with low solubility in water. Owing to the good adhesion of the ionic polymers and of the substances which are used in the formation of the mixed salts, the statins present in the mixed salts also adhere better to the surface of the dental implant materials than statins alone, it being possible to apply the mixed salts as a dry coating.

For example, the lactone form of simvastatin dissolves in ethanol and in an ethanol/water mixture with at least 50% ethanol; the open-chain acid form of simvastatin, in contrast, dissolves in an ethanol/water mixture with only 25% ethanol.

The release of a low molecular weight active ingredient from an implant coating to the surrounding aqueous medium is determined essentially by the diffusion thereof out of the coating. The diffusion in turn depends on the solubility of the active ingredient in the surrounding aqueous medium. As a result of the conversion of the water-insoluble lactone form of simvastatin to the water-soluble open-chain dihydroxy acid form, it is to be expected that simvastatin, owing to its better solubility, is rapidly absorbed and transported away from the physiological environment of the dental implant, and therefore no retarding action can set in at the site of action. One of the fundamental ideas of the invention is therefore to convert the biologically active but water-soluble open-chain form of simvastatin (or active ingredient) to a sparingly soluble salt form which can be applied as a dry layer. The availability of the active ingredient is determined by a solubility equilibrium between the free active ingredient and the active ingredient present as a constituent of a sparingly soluble salt. The diffusion of the active ingredient is therefore preceded by a solubility equilibrium, this equilibrium replacing the diffusion as the rate-determining step. It is therefore important for the retarded release of the simvastatin (or of the statins in general) that they form sparingly water-soluble salts with appropriate cationic reaction partners, like the water-soluble ionic polymers or amino-containing compounds detailed in the invention.

In the said salts of the open-chain dihydroxy acid form of simvastatin (of the statins in general) and the amino-containing water-soluble ionic polymers or low molecular weight amino-containing compounds, the simvastatin (statin in general) constitutes the anionic component, and the amino-containing water-soluble ionic polymers or low molecular weight amino-containing compound constitutes the cationic component. These salts can be used as a coating for metallic or nonmetallic surfaces on dental implants.

The coating of the dental implants with these salts can, according to the prior art, be applied directly to the dental implant without use of an intermediate layer or of an additional support. The coating therefore consists essentially or completely of the mixed salts already discussed.

The dental implants used for the coatings may be dental implants made of calcium carbonate, calcium sulfate, calcium phosphate ceramics, glass ceramics, bioglass, organic materials or composites of the materials mentioned, and dental implants made from pure titanium, titanium alloys, alloys of cobalt and chromium or stainless steel, or dental implants made from native constituents such as gelatin, collagen or allogenic materials. Further nonmetallic materials which are suitable for such a coating process are aluminum oxide ceramics and zirconium oxide ceramics. These dental implants may have a smooth, porous and/or roughened surface. The surface structure can be produced by mechanical methods (e.g. sandblasting) and/or chemical methods (e.g. acid treatment, salt melt treatment), though the use of structured surfaces is preferable.

The corresponding material surfaces can be coated by employing different coating methods, such as dipping, spraying or dripping. In these processes, the evaporation or vaporization of the suspension medium or solvent forms a simvastatin-containing (generally statin-containing) coating with only sparing solubility in water.

According to the invention, the said mixed salts of simvastatin (statin in general) and the amino-containing water-soluble ionic polymers or low molecular weight amino-containing compounds are used for the coating process in the form of finely distributed suspensions of water or as solutions in volatile organic solvents, for example of alcohols or chloroform.

The coated implants can be dried by a known drying process, i.e. for example, by drying at elevated temperature and/or drying under reduced pressure or by drying in a gas stream.

The coating described in the invention is preferably notable in that, after operative insertion with the implant into the human or animal tissue or the bone, it releases the simvastatin (statin in general) in a retarded manner over a prolonged period to the immediate environment of the implant, as a result of which the implant can achieve its effect there.

Ways of Performing the Invention

Preparation of the Dihydroxy Acid Form of Simvastatin

To form the sparingly water-soluble salts of simvastatin with the ionic polymers discussed (or the unsaturated alkyl compounds with amino groups), the simvastatin must be converted to the acid form. This involves converting the lactone form of simvastatin to the open-chain, biologically active dihydroxy acid form.

25 mg (59.72 µmol) of simvastatin in the lactone form are dissolved in 0.625 ml of ethanol and, after adding 0.9375 ml of 0.1 N sodium hydroxide solution, stirred at 50° C. for 2 hours. After cooling to room temperature, the pH of this solution is adjusted to 2.5 or 7.2 with a 0.1 N hydrochloric acid solution. The open-chain acid form is obtained from this solution by extracting with chloroform (5×2.5 ml) with the aid of a saturated sodium chloride solution. After drying the chloroform with sodium sulfate (for 1 hour), the chloroform is removed on a rotary evaporator and the clear product is dried under reduced pressure (10 mbar). The simvastatin is then dissolved in 2.5 ml of ethanol or 5 ml of an ethanol-water mixture (1:1). To completely dissolve the acid form of simvastatin which had been adjusted to pH 7.2, it had to be stirred at 50° C. for 18 hours.

Alternatively, the open-chain simvastatin, after the adjustment of the pH to 7.2, can also be used without extraction with chloroform, after being made up to 2.5 ml with water.

Characterization of the Open-chain, Biologically Active Dihydroxy Acid Form of Simvastatin:

NMR data: $^1$H NMR (methanol-d4, deuterium oxide): 6.0 (d, 1H, CH); 5.8 (m, 1H, CH); 5.5 (m, 1H, CH), 5.3 (d, 1H, CH); 4.9-5.1 (3 s overlapping, broad, approx. 3H, OH); 4.1 (m, 1H, CH); 3.7 (m, 1H, CH), 2.25-2.5 (3 m overlapping, 4H, $CH_2$ and CH); 1.9-2.05 (m, 1H, CH); 1.45-1.7 (4 m, overlapping, 7H, CH and $CH_2$); 1.15-1.45 (2 m, 4H, $CH_2$); 1.1 (2 s overlapping, 6H, $CH_3$); 0.95 (d, 3H, $CH_3$); 0.9 (d, 3H, $CH_3$); 0.8 (d, 3H, $CH_3$); $^{13}$C NMR: 181.1: C (quat.); 180.8: C (quat.); 134.8: CH; 133.0: C (quat.); 130.5: CH; 129.5: CH; 71.5: CH; 70.6: CH; 68.9: CH; 49.2: CH; 45.7: $CH_2$; 44.8: $CH_2$; 44.3: C (quat.); 38.3: CH; 38.2: $CH_2$; 35.3: $CH_2$; 34.1: $CH_2$; 33.4: CH; 28.3: $CH_2$; 25.7: CH; 25.2: $CH_3$; 25.2: $CH_3$; 23.6: $CH_3$; 14.1: $CH_3$; 9.9: $CH_3$.

IR data: wavenumbers of characteristic bands [1/cm]: 3360 (—OH VV); 3018 (=C—H VV); 2966 (—C—H VV); 2933 (—$CH_2$ VV); 2872 (—$CH_3$ VV); 1718 (—C=O VV); 1571 (—C—O VV in carboxylic acids); 1400 (—$CH_3$— and $CH_2$ DV); 1313 (—C—O VV in carboxylic acids); 1262 (—C—O—C VV); 1161 (—C—O VV); 1126 (—C—O VV); 1057 (—C—O VV); 860 (=C—H VV); (VV: valence vibration; DV: deformation vibration).

Preparation of a Simvastatin Diethylaminodextran Salt 25 mg (59.72 µmol) of simvastatin which has been converted to the open-chain acid form and adjusted to pH 7.2 without extraction with chloroform are initially charged dissolved in a total volume of 2.5 ml, and 27.47 mg (119.44 µmol) of diethylaminoethyldextran (degree of substitution: 0.5) dissolved in 0.625 ml of ethanol and 1.8725 ml of water are added to this solution. The milky white suspension which forms is stirred at room temperature for 18 hours. Subsequently, the suspension is centrifuged at 14 000 rpm for 10 min. The clear supernatant is removed, and the precipitate is washed with distilled water and dried in a desiccator under reduced pressure (10 mbar) at room temperature for 2 days. The end product was obtained with a yield of 77.1%.

Preparation of Simvastatin-chitosan 25 mg (59.72 µmol) of the open-chain acid form of simvastatin (adjusted to a pH of 7.2 without chloroform extraction) are dissolved as a 1% solution in 1% acetic acid in a mixture of 25% ethanol and 75% water, as is chitosan. 0.962 ml of the chitosan solution, i.e. 9.62 mg (59.72 µmol) of chitosan, is added to the simvastatin solution. The fibrous precipitate which forms is stirred at room temperature for a further 18 hours, centrifuged off (10 min; 14 000 rpm) and washed with distilled water. The precipitate thus treated is dried in a desiccator under reduced pressure (10 mbar) for at least 2 days. The yield of simvastatin-chitosan achieved is 73.9%.

Characterization of a Salt of the Open-chain Acid Form of Simvastatin and Chitosan IR data: wavenumbers of characteristic bands [1/cm]: 3375 (—OH VV); 2967 (—C—H VV); 2931 (—$CH_2$ VV); 2877 (—$CH_3$ VV); 1716 (—C=O VV); 1560 (—C—O VV in carboxylic acids, —NH DV, overlapping); 1390 (—$CH_3$ DV); 1313 (—C—O VV in carboxylic acids); 1260 (—C—O—C VV); 1158 (—C—O VV); 1058 (—C—O VV); 861 (=C—H VV); (VV: valence vibration; DV: deformation vibration).

Preparation of a Salt of Simvastatin, Diethylaminoethyldextran and Carboxymethylcellulose After conversion of simvastatin to the open-chain acid form, adjustment of the pH 2.5 and extraction with chloroform, it is dissolved in 3.75 ml of a solution of 50% ethanol and 50% water. Solutions of 27.47 mg (119.44 μmol) of diethylaminoethyldextran (degree of substitution: 0.5) in 1.25 ml of water and 15 mg (71.13 μmol) of carboxymethylcellulose (degree of substitution: 0.84) in 1.25 ml of water are added to this solution (simvastatin:diethylaminoethyldextran:carboxymethylcellulose ratio=1:1:1 taking account of the degrees of substitution), which produces a white precipitate. The suspension is stirred at room temperature for 18 hours. After centrifugation (10 min; 14 000 rpm) the clear supernatant is removed and the precipitate is washed with distilled water. The resulting product is dried under reduced pressure in a desiccator for at least 2 days. The simvastatin:diethylaminoethyldextran:carboxymethylcellulose ratio was varied from 1:1:1 through 1:1:2 to 2:2:1. The yields of the particular batches are 65.6% for 1:1:1, 56.4% for 1:1:2 and 41.0% for 2:2:1.

Preparation of a Simvastatin-octadecylamine Salt 25 mg (59.72 μmol) of simvastatin which has been converted to the open-chain acid form with ethanolic sodium hydroxide solution in 0.625 ml of ethanol is dissolved in a total volume of 2.5 ml of ethanol. After adding 16.1 mg (59.72 μmol) of octadecylamine, dissolved in 2.5 ml of ethanol, the mixture is stirred at room temperature for 24 hours. Subsequently, 5 ml of distilled water are added and the mixture is stirred at room temperature for a further 2 hours. Once the precipitate formed has been centrifuged off (10 min; 14 000 rpm), it is dried in a desiccator under reduced pressure (10 mbar) at room temperature for at least 2 days. The yield of simvastatin-octadecylamine is 32.3%.

Characterization of a Salt of the Open-chain Acid Form of Simvastatin and Octadecylamine IR data: wavenumbers of characteristic bands [1/cm]: 3331 (—NH VV); 2956 (—CH$_3$ VV); 2917 (—CH$_2$ VV); 2850 (—CH$_2$ VV); 1719 (—C=O VV); 1647 (—NH DV); 1570 (—C—O VV in carboxylic acids, —NH DV, overlapping); 1487 (RV); 1472 (—CH$_3$ and CH$_2$ DV); 1392 (—CH$_2$ DV); 1317 (—C—O VV in carboxylic acids); 1158 (—C—O VV); (VV: valence vibration; DV: deformation vibration; RV: ring vibration).

Coating of Dental Implants

The surface of dental implants made from titanium or a titanium alloy is roughened by means of a sandblasting and acid etching process in the regions which are in contact with the bone. To produce a suspension of the above-described simvastatin-octadecylamine salt, 41 mg of the simvastatin-octadecylamine salt are distributed in 1 ml of ethanol while stirring within 10 min. Treatment with an ultrasound homogenizer (total power 20 watts) affords a homogeneous suspension.

After the dental implants have been heated to 70° C., they are sprayed repeatedly with appropriate amounts of the suspension described using a conventional spray gun. During this spray operation, the implants which have been clamped in a suitable device rotate uniformly about their longitudinal axis. After the end of each and every spray operation, the dental implants are dried at 70° C. until the suspension medium has evaporated completely.

When the dental implants are coated with the simvastatin-diethylaminoethyldextran salt, 10 mg of this salt are dissolved in 1 ml of ethanol while stirring at 50° C. within 5 min. A solution of 10 mg of chitosan in 1 ml of a mixture of ethanol and water (75% by vol./25% by vol.) with an acetic content of 1% is added to this solution, and diluted with 4 ml of a 1% acetic acid solution in methanol. The resulting viscous solution is homogenized with an ultrasound homogenizer (total power 20 watts) and sprayed onto the heated dental implants as described above.

The implants thus produced exhibited both better performance in vitro and better incorporation performance in vivo.

The invention claimed is:

1. A process for producing an implant having a coating which, in the implanted state, is in at least some of the surface regions which are in at least indirect contact with hard and/or soft tissue,
   said coating comprising a statin in the form of a pharmaceutically compatible salt which has been derived from an open-chain, biologically active dihydroxy acid form and
   has at least one further component selected from the group of: of the branched or linear, substituted or unsubstituted, saturated or partly unsaturated C10-C30 alkyl-, alkenyl-, alkylaryl-, aryl-, cycloalkyl-, alkylcycloalkyl- or alkylcycloarylamines or mixtures thereof,
   and/or
   at least one water-soluble ionic polymeric component,
   said process comprising the following steps:
   (1) preparation of a first suspension or first solution of a dihydroxy acid form of the statin in a suitable solvent;
   (2) preparation of a second suspension or a second solution of said at least one further component and/or of said water-soluble ionic polymeric component;
   (3) mixing said first and second solution and/or suspension to form a suspension and/or solution of the statin and of said at least one further component and/or of the statin and of the water-soluble ionic polymeric component and in a precipitating the statin and said at least one further component and/or the statin and the water-soluble ionic polymeric component in a precipitation reaction to form a precipitation product;
   (4) isolating the precipitation product as a mixed salt;
   (5) dissolving or suspending this mixed salt in a solvent or suspension medium to form a mixed salt solution or mixed salt suspension;
   (6) applying the mixed salt solution or mixed salt suspension to the implant surface to be coated by spray application, dropwise application or dipping, and
   (7) removing the suspension medium or solvent to form a low-water-solubility, statin-containing, dry coating.

2. The process as claimed in claim 1, wherein the concentrations of the mixed salt suspension(s) and/or mixed salt solution(s) which comprise the statin and/or the at least one further component and/or at least one ionic polymeric component are selected such that the statin and the at least one further component and/or at least one ionic polymeric component are present in the coating formed by in situ salt formation in a ratio of 10:1 to 1:5.

3. The process as claimed in claim 1, wherein the suspension medium or solvent for the formation of the mixed salt solution or mixed salt suspension is a suspension medium or solvent mixture.

4. The process as claimed in claim 1, wherein the suspension medium or solvent for the formation of the mixed salt solution or mixed salt suspension is water or one or more organic suspension media or solvents, selected from the group of: chloroform as the suspension medium, ethanol or methanol as the solvent, or mixtures of these systems where chemically possible.

5. The process as claimed in claim 1, wherein the statin is a component selected from the group of: atorvastatin, cerivastatin, fluvastatin, lovastatin, pitavastatin, pravastatin or rosuvastatin, mevastatin, squalestatin, simvastatin, and mixtures thereof.

6. The process as claimed in claim 1, wherein the statin is simvastatin.

7. The process as claimed in claim 1, wherein the statin and the at least one further component and/or the at least one water-soluble ionic polymeric component are present in the coating as a complex or mixed salt with low solubility in water.

8. The process as claimed in claim 7, wherein the complex or the mixed salt has a solubility in pure water of less than 1 mg/ml at room temperature.

9. The process as claimed in claim 1, wherein the at least one further component is at least one unbranched, unsubstituted, C10-C20 alkylamine, and/or the alkali metal or alkaline earth metal salt thereof.

10. The process as claimed in claim 1, wherein the at least one further component is an amphiphilic component which has cationic character, and bears a single positive charge.

11. The process as claimed in claim 1, wherein in step 1. and in the final coating the statin is present in the free dihydroxy acid form and at least partly in the alkali metal, alkaline earth metal, ammonium and/or magnesium salt form and/or salt form with the further component as the ammonium cation.

12. The process as claimed in claim 1, wherein the at least one water-soluble ionic polymeric component is a polymeric component with free cationic groups.

13. The process as claimed in claim 1, wherein the at least one water-soluble ionic polymeric component comprises amino-containing derivatives of natural polysaccharides.

14. The process as claimed in claim 1, wherein the statin present in the free dihydroxy acid form in the final coating and the at least one further component selected as the alkylamine are present in the coating in a molar ratio between 2:1 to 1:2.

15. The process as claimed in claim 1, wherein the statin selected in the free dihydroxy acid form and the water-soluble ionic polymeric component in the coating are present in a molar ratio between 2:1 to 1:2, based in each case on the carboxyl groups of the statin used in the free dihydroxy acid form and the cationic groups present in the polymeric component.

16. The process as claimed in claim 1, wherein the coating is applied to a smooth, porous and/or roughened surface without a carrier, the implant consisting at least partially or in sections of metal and/or ceramic and/or polymers and/or being of native origin, and the coating being applied directly and without an intermediate layer to such an implant, and the implants comprising calcium phosphate ceramics, aluminum oxide and zirconium oxide ceramics, bioglass, glass ceramics, calcium carbonate, calcium sulfate, organic polymers or composites of the materials mentioned, or surfaces of metallic implants made from pure titanium, titanium alloys, cobalt-chromium alloys or stainless steel, or native implant surfaces which consist of collagen, gelatin or materials of allogenic origin.

17. The process as claimed in claim 1, wherein the thickness of the coating is between 0.5-5 μm, and the coating is a dry, essentially solvent-free coating which is essentially water-free before implantation.

18. The process as claimed in claim 1, wherein in step 6. the coating is applied as a slurry or suspension in an organic solvent, or in an organic solvent in a mixture with water, in a dipping or spraying process, and is then dried substantially completely.

19. A process for producing an implant according to claim 1, wherein in the step (1) of mixing a dihydroxy acid form of the statin dissolved in a suitable solvent, alcohol is used or an alcohol-water mixture in a ratio of 25:75.

20. A process for producing an implant according to claim 1, wherein the step (2) involves dissolving of the at least one further component and/or at least one water-soluble ionic polymeric component in alcohol or an alcohol-water mixture.

21. A process for producing an implant according to claim 1, wherein in the step (7) of removing the suspension medium or solvent this is effected by evaporation or vaporization, to form a low-water-solubility, statin-containing, dry coating.

22. A process for producing an implant according to claim 1, wherein the at least one further component is selected from the group of: branched or linear, substituted or unsubstituted, saturated or partly unsaturated C10-C30 alkyl-, alkenyl-, alkylaryl-, aryl-, cycloalkyl-, alkylcycloalkyl- or alkylcycloarylamines or mixtures thereof.

23. The process as claimed in claim 1, wherein the concentrations of the mixed salt suspension(s) and/or mixed salt solution(s) which comprise the statin and/or the further component and/or ionic polymeric component are selected such that the statin and the further component and/or ionic polymeric component are present in the coating formed by in situ salt formation in a ratio between 2:1 and 1:2.

24. The process as claimed in claim 7, wherein the complex or the mixed salt has a solubility in pure water in the range of 0.05-0.9 mg/ml at room temperature.

25. The process as claimed in claim 1, wherein the at least one further component is selected from the following group: decylamine, tetradecylamine, hexadecylamine, octadecylamine, dodecylamine.

26. The process as claimed in claim 1, wherein the at least one water-soluble ionic polymeric component comprises amino-containing derivatives of natural polysaccharides selected from the group of: dextran, cellulose, starch, pullulan or chitosan, or mixtures thereof.

27. The process as claimed in claim 1, wherein the at least one water-soluble ionic polymeric component is a polymeric component with free cationic groups, namely a polymeric component which derives from biologically compatible biopolymers.

28. The process as claimed in claim 1, wherein the at least one water-soluble ionic polymeric component comprises amino-containing derivatives of natural polysaccharides.

* * * * *